United States Patent
Wei et al.

(10) Patent No.: US 6,245,729 B1
(45) Date of Patent: Jun. 12, 2001

(54) PERACID FORMING SYSTEM, PERACID FORMING COMPOSITION, AND METHODS FOR MAKING AND USING

(75) Inventors: G. Jason Wei, Mendota Heights; David D. McSherry, Minneapolis, both of MN (US)

(73) Assignee: Ecolab, Inc., St. Paul, MN (US)

( * ) Notice: Subject to any disclaimer, the term of this patent is extended or adjusted under 35 U.S.C. 154(b) by 0 days.

(21) Appl. No.: 09/361,843

(22) Filed: Jul. 27, 1999

(51) Int. Cl.$^7$ .............................. C11D 3/395; C11D 3/48; C11D 9/50; C11D 17/00
(52) U.S. Cl. .................. 510/376; 510/378; 510/382; 510/439
(58) Field of Search .................... 510/367, 370, 510/376, 378, 382, 439

(56) References Cited

U.S. PATENT DOCUMENTS

| | | |
|---|---|---|
| 3,639,248 | 2/1972 | Moyer et al. . |
| 3,906,926 | 9/1975 | Staples . |
| 4,159,316 | 6/1979 | Januszewski et al. . |
| 4,186,746 | 2/1980 | Byler . |
| 4,259,383 | 3/1981 | Eggensperger et al. . |
| 4,338,098 | 7/1982 | Yamaji . |
| 4,391,724 | 7/1983 | Bacon . |
| 4,391,725 | 7/1983 | Bossu . |
| 4,497,757 | 2/1985 | Beimesch et al. . |
| 4,585,843 | 4/1986 | Flesher et al. . |
| 4,702,853 | 10/1987 | Benson et al. . |
| 5,296,239 | 3/1994 | Colery et al. . |
| 5,409,632 | 4/1995 | Showell et al. . |
| 5,462,692 | 10/1995 | Roesler et al. . |
| 5,505,740 | 4/1996 | Kong et al. . |
| 5,536,435 | 7/1996 | Chapman et al. . |
| 5,585,174 | 12/1996 | Levitsky et al. . |
| 5,607,684 | 3/1997 | Lew et al. . |
| 5,635,462 | 6/1997 | Fendler et al. . |
| 5,670,466 | 9/1997 | Sivik et al. . |
| 5,736,497 | 4/1998 | Steiner . |
| 5,747,004 | 5/1998 | Giani et al. . |
| 5,753,138 | 5/1998 | Watson et al. . |
| 5,827,915 | 10/1998 | Saita et al. . |

FOREIGN PATENT DOCUMENTS

| | | |
|---|---|---|
| 861 276 | 3/1978 | (BE) . |
| 28 28 724 A1 | 1/1980 | (DE) . |
| 1 571 357 | 7/1980 | (DE) . |
| 0 488 090 A1 | 6/1992 | (EP) . |
| WO 94/11483 | 5/1994 | (WO) . |
| WO 94/18297 | 8/1994 | (WO) . |

Primary Examiner—Yogendra Gupta
Assistant Examiner—John M. Petruncio
(74) Attorney, Agent, or Firm—Merchant & Gould P.C.

(57) ABSTRACT

A system for forming and releasing an aqueous peracid solution is disclosed. The system includes a container and a peracid forming composition provided within the container. The container is permeable to the passage of water and aqueous peracid solution. The peracid forming composition includes a peracid precursor and a peroxygen source. Preferably, the peracid forming composition includes a chemical heater capable of releasing heat upon hydration. When placed in water, water enters the container and interacts with the peracid forming composition provided within the container. The water combines with the peracid precursor and peroxygen source to provide an aqueous peracid composition. The presence of a chemical heater within the container provides for the generation of heat within the container which enhances the rate of peracid formation. The peracid solution leaves the container and forms an effective sanitizing amount of sanitizer. A composition for forming and releasing an aqueous peracid solution is disclosed. The composition can include a mixture of peracid forming components or a composite structure containing peracid forming components adhered together. Methods of sanitizing a surface having a population of microorganisms are provided, and methods for manufacturing are provided.

14 Claims, 3 Drawing Sheets

PERACID FORMING SYSTEM, PERACID FORMING COMPOSITION, AND METHODS FOR MAKING AND USING

FIELD OF THE INVENTION

The invention relates to a system for forming and releasing an aqueous peracid solution; a composition for forming and releasing an aqueous peracid solution; a method of sanitizing a surface having a population of microorganisms; and a method for manufacturing an article and composition. The system includes a peracid forming composition provided within a container permeable to the passage of water and aqueous peracid sanitizer solution. The composition can be a peracid forming composition including peracid precursor, peroxygen source, and chemical heater. In addition, the composition can include composite structures which include both peracid precursor and peroxygen source adhered together within a composite structure. The method of sanitizing includes a step of combining the system and/or the composition with water to generate an aqueous peracid sanitizer solution and sanitizing a surface having a population of microorganisms.

BACKGROUND OF THE INVENTION

Numerous classes of chemical compounds exhibit varying degrees of antimicrobial or biocidal activity. Antimicrobial compositions are particularly needed in the food and beverage industries to clean and sanitize processing facilities such as pipelines, tanks, mixers, etc. and continuously operating homogenization or pasteurization apparatus. Sanitizing compositions have been formulated in the past to combat microbial growth in such facilities. For example, Grosse-Böwing et al., U.S. Pat. Nos. 4,051,058 and 4,051,059, teach peracetic acid materials. These peroxy-containing compositions are known for use in the production of microbiocidal agents. One such composition disclosed by Grosse-Böwing et al. contains peracetic acid, acetic acid or mixtures of peracetic and acetic acid, hydrogen peroxide, anionic surface active compounds such as sulfonates and sulfates, and water. Wang, U.S. Pat. No. 4,404,040, teaches a short chain fatty acid sanitizing composition comprising an aliphatic short chain fatty acid, a hydrotrope solubilizer capable of solubilizing the fatty acid in both the concentrate and use solution, and a hydrotrope compatible acid so that the use solution has a pH in the range of 2.0 to 5.0.

Peracetic acid has been shown to be a good biocide, but only at fairly high concentrations (generally greater than 100 part per million (ppm)). Similarly, peroxyfatty acids have also been shown to be biocidal, but only at high concentrations (greater than 200 ppm), such as in the composition disclosed in European Patent Application No. 233,731. Antimicrobial compositions having low use concentrations (less than 100 ppm) which effectively kill microbes are particularly desirable. Low concentrations minimize use cost, surface corrosion, odor, carryover of biocide into foods and potential toxic effects to the user. Therefore, a continuing need exists to provide such an antimicrobial composition for use in food processing, food service and health care facilities.

Combining a peroxygen source with an acid precursor in forming bleaching compositions or sanitizing compositions has been disclosed in the prior art. The prior art compositions are often formed in an aqueous solution which can be unstable, short lived, corrosive, and difficult to contain due to a need to vent the container containing the aqueous solution. Such compositions require high purity because impurities can catalyze decomposition of the peracid material. Aqueous solutions also require shipping of water which increases costs.

U.S. Pat. No. 5,296,239 to Colery, et al. and U.S. Pat. No. 5,736,497 to Steiner describe aqueous liquid peracid sanitizer formulations. International Publication No. WO 94/11483 describes the use of acylated citrate esters and ethoxylated alcohols as stabilizers. Solid mixtures are also known that generate peracid upon dissolution in aqueous media. U.S. Pat. No. 5,505,740 to Kong, et al. describes in situ formation of peracid where the aqueous wash solution is initially raised to a relatively high pH level by introduction of an alkaline agent for enhancing production of the peracid in the aqueous solution, then lowering the pH of the aqueous solution for enhancing bleach performance.

Aqueous peroxygen solutions containing perborates and/or hydrogen peroxide in combination with acids (e.g., boric acid) are often stabilized by the addition of a stabilizing agent. Stabilizing agents described in the prior art include carbazole sulfonates, diphenylamine sulfanates, N-phenylamino naphthalene sulfonates, and diethylenetriamine pentamethylene phosphonic acid. See U.S Pat. No. 5,736,497 to Steiner. This patent additionally describes the stabilization of alkaline hydrogen peroxide solutions by the addition of an organic stannate. U.S. Pat. No. 5,296,239 to Colery et al. describes stabilizing a thickened peracetic composition by adding sequestering agents, free-radical scavengers, and mixtures of sequestering agents and free-radical scavengers.

Techniques for enhancing performance of preformed peracids have been disclosed by a number of prior art references. In particular, U.S. Pat. No. 4,391,725 to Bossu discloses a granular hydrophobic peroxyacid laundry product in the form of a preformed peracid bleach provided within a pouch. An acid additive, indicated as having a pKa of from about 2 to about 7, is combined with the hydrophobic peracid in the pouch in order to aid in release of the peracid from the pouch, thereby enhancing bleach performance. U.S. Pat. No. 4,391,723 to Bacon et al. and U.S. Pat. No. 4,391,724 to Bacon describe the inclusion of boric acid or other acids together with the preformed peracids for improving bleach performance.

SUMMARY OF THE INVENTION

A system for forming and releasing an aqueous peracid solution is provided by the invention. The system includes a peracid forming composition and a container for containing the peracid forming composition. The peracid forming composition includes a peracid precursor and a peroxygen source. Preferably, the peracid forming composition includes a chemical heater capable of releasing heat upon hydration. The chemical heater can increase the local temperature within the container by at least about 5° C. after the system is placed in water. The local temperature is considered the temperature of the environment within the container. The temperature increase is measured from the ambient temperature of the water in which the system is immersed. The container is permeable to the passage of water and aqueous peracid solution. When the system is immersed in water, water flows into the container, and the peracid forming composition generates peracid which flows out of the container providing an aqueous peracid sanitizer solution having a pH of less than 8.

The peracid precursor is preferably a component which is relatively nonreactive with the peroxygen source under temperature conditions normally found during transportation and storage. Preferred peracid precursors which can be used according to the invention include carboxylic acid anhydrides such as glutaric acid anhydride, succinic acid anhydride, maleic acid anhydride and mixtures thereof. The peroxygen source is preferably a component which remains relatively nonreactive with peracid precursor under temperature conditions normally encountered during the storage and shipment. A preferred peroxygen source includes sodium perborate. It should be appreciated that while the peracid precursor and peroxygen source are characterized as relatively nonreactive toward each other, this is under conditions of storage and transport. The peracid precursor and peroxygen source are preferably very reactive toward each other when combined with water (liquid or vapor). The chemical heater can be any material which is compatible (preferably nonreactive) with the peracid precursor and peroxygen source, and which increases the temperature of the environment within the container when combined with water. Preferably, the chemical heater is included in an amount sufficient to increase the local temperature by at least about 5° C. after introducing the system into water. Exemplary chemical heaters include hydratable salts such as salts of inorganic and organic acids, salts of mineral acids, magnesium sulphate, alkaline earth metal salts, and alkali metal salts, and alkaline earth metal oxides.

A composition for forming and releasing an aqueous peracid solution is provided by the invention. The composition can take several forms. One form of the composition includes a mixture of components. For example, the mixture can include about 2 wt % to about 30 wt % of a carboxylic acid anhydride, about 2 wt % to about 30 wt % of a peroxygen source, and about 10 wt % to about 60 wt % of a chemical heater capable of releasing heat upon hydration. Another form of the composition includes a composite structure which can take the form of granules, blocks, tablets, and the like. The composite structure includes peracid precursor and peroxygen source adhered together within the composite structure. A binder holds the peracid precursor and peroxygen source together within each composite structure. The peracid precursor can function as the binder for holding the peracid precursor and peroxygen source together within the composite structure. The binder can include other components such as alcohol ethoxylates and polymers (homopolymers and/or copolymers) of ethylene oxide and/or propylene oxide. The composite structure can additionally include a chemical heater, an acid catalyst, viscosity modifier, a moisture barrier, and combinations thereof.

The composition can be referred to as a peracid forming composition because it includes peracid forming components which react, in the presence of water, to generate an aqueous peracid solution. The composite structure and/or the mixture of peracid forming components can be provided within the container permeable to the passage of water and aqueous peracid solution. It is expected, however, the composite structure will be used without a permeable container. That is, the composite structure will be applied to a wetted surface and the peracid solution will form on the wetted surface. In contrast, it is expected that the mixture of peracid forming components will generally be used to provide a quantity of aqueous peracid solution which can then be used for various applications.

Methods of sanitizing a surface having a population of microorganisms is provided by the present invention. The method includes a step of combining the system for forming and releasing an aqueous peracid sanitizer solution with water, or combining the composite structure for forming and releasing an aqueous peracid sanitizer solution with water. The system can be used for generating a volume of aqueous peracid sanitizer solution. This solution can be provided, for example, in a bucket or container. The sanitizer solution is particularly useful for use in hard surface disinfection, potable water disinfection, fruit/veggie sanitizing rinse, medical instrument sanitization, and kitchen sanitization. The composite structure can be used by scattering the composite granules on a wet surface which is to be treated. The aqueous peracid solution is then generated on the surface. The composite structure can preferably be used in various applications including biohazard cleanup, carpet sanitization, floor sanitization, and ostomy deodorization.

Methods for manufacturing a system for forming and releasing an aqueous peracid solution and for manufacturing composite structures for forming and releasing an aqueous peracid solution are provided by the invention. The methods for manufacturing a system for forming, and releasing an aqueous peracid solution can include the steps of providing a peracid forming composition within a container, and providing a moisture barrier envelope around the peracid forming composition within the container. The moisture barrier envelope is provided for reducing contact of the peracid forming composition with liquid or vapor water. The methods for manufacturing composite structures for forming and releasing an aqueous peracid solution can include a step of adhering peracid precursor and peroxygen source together to provide a composite structure including both peracid precursor and peroxygen source adhered together. The composite structure can include a chemical heater and/or acid catalyst as part of the structure. In general, the adhesion of the components together will be accomplished with a binder. The peracid precursor can function as the binder. In addition, a moisture barrier coating can be provided around the composite structures, and/or around the peracid precursor component, the peroxygen source components, or both components separately.

DETAILED DESCRIPTION OF THE INVENTION

The invention relates to a system for forming and releasing an aqueous peracid solution. The system includes a container for containing or holding the peracid forming composition, but which is permeable to the passage of water and aqueous peracid solution. The peracid forming composition is provided so that it remains relatively stable during conditions of storage, but under conditions of use, such as when liquid water is introduced into the composition, the peracid forming composition generates an aqueous peracid solution. The system and composition are preferably "shelf stable" which means that under storage conditions of ambient temperature, at least about 80 percent remains active after three months. Preferably, at least about 80 percent remains active after about six months. It should be understood that the level of activity is based upon an activity of 100 percent immediately after product formation.

When it is desirable to generate an aqueous peracid solution, the system can be placed in a quantity of water. The water then flows through the permeable container and contacts the peracid forming composition resulting in the generation of aqueous peracid solution which flows out of the container and into the surrounding water.

After a period of time, the quantity of water contains a sufficient amount of peracid to provide an aqueous peracid sanitizer solution for sanitizing the surface having a microbial population.

The peracid forming composition can be referred to as a self-heating peracid forming composition when it includes at least one component which is responsible for the generation of heat. Applicants have found that by providing localized heating, the rate of peracid formation increases. A chemical heater can be used which is activated by water and which increases the local temperature within the container to increase the rate of peracid formation. A preferred chemical heater is one which generates heat upon contact of the peracid forming composition with water.

It should be understood that the phrase "aqueous peracid sanitizer solution" refers to the aqueous solution which can be used for sanitizing, disinfecting, and/or bleaching the surface of a substrate. The aqueous peracid sanitizer solution can be referred to more simply as the sanitizer solution or as the use solution. Accordingly, the sanitizer solution can be provided with any desired concentration of peracid sufficient to provide the desired degree of sanitizing, disinfecting, and/or bleaching. The "peracid forming composition" refers to the composition which, when combined with water, generates sanitizer solution.

The peracid forming composition includes, as reactants, a peracid precursor and a peroxygen source. The composition can be provided in the form of a solids mixture, a combination of solid and liquid, and as composite structure. In the case of a solids mixture, the peracid precursor and peroxygen source are preferably both provided as solids which do not react together until contacted with water. The solids mixture includes a mixture of solid peracid precursor, preferably in powder form, with solid peroxygen source, preferably in powder form. When the composition is provided in the form of a combination of solid and liquid components, the solid and liquid components are preferably separated. For example, the liquid component can be contained within a rupturable container. Once the container is ruptured, the solid component and the liquid component can react to form aqueous peracid solution. Alternatively, the liquid component can be absorbed onto a substrate so that it can be mixed with the solid component without substantially reacting with the solid component. In addition, the liquid component which has been absorbed onto a substrate can be coated with a moisture barrier coating to help prevent reaction until the moisture barrier coating is removed or penetrated. The composite structure contains both the peracid precursor and the peroxygen source bound together in a single construction. The composite structure can be provided in the form of granules, blocks, tablets, and the like. When the composite structure is contacted with water, the peracid precursor component and peroxygen source component within the composite structure react to form the peracid sanitizer solution. A component of the composite structure can be a liquid component which has been absorbed onto a substrate and optionally coated with a moisture barrier coating to help prevent reaction until the moisture barrier coating is removed.

Components in addition to the peracid precursor and peroxygen source can be incorporated into the peracid forming composition. The additional components include acid catalysts, chemical heaters, viscosity modifiers, and binders.

An acid catalyst can additionally be incorporated into the peracid forming composition to provide the aqueous peracid sanitizer solution with a pH of below about 8 (and preferably below about 7) and/or to increase the rate of forming aqueous peracid solution. In general, pH values below about 7 are desirable for providing a sanitizer solution capable of killing microorganisms. It should be understood that reference to pH values refers to the pH of the sanitizer solution or use solution. The pH value of a peracid solution within the container may, at times, be relatively acidic. The peracid solution flows out of the container and mixes with the remaining water environment to provide a sanitizer solution or use solution having a pH of below about 8.

It is advantageous for the components of the peracid forming composition to remain solid under normal storage conditions. This is particularly true when the peracid forming components are provided in contact with each other within the permeable container because it is desirable that the components do not react together until contacted with water. Although a preferred embodiment of the invention contemplates the entire peracid forming composition as a solid composition, it is possible for at least one of the components to be a liquid component. For example, the liquid component can be provided within another container. Once the container is ruptured, the contents thereof can then combine with the remaining peracid forming components to generate peracid sanitizer solution. The container can be ruptured by pressure such as the pressure generated by a human hand. Alternatively, a liquid component can be absorbed onto an absorbent or substrate which will reduce reactions between the acid precursor and the peroxygen source until water is introduced. Furthermore, the liquid component absorbed onto an absorbent or substrate which can be coated with a barrier material which dissolves in the presence of water.

The peracid forming composition can be provided in the form of granules or particles which include both peracid precursor and peroxygen source together in the granules or particles. A binder can be used for holding the peracid precursor and peroxygen source together in the granules or particles. It should be understood that the phrase "composite structure" indicates that at least a portion of the structure includes, in combination, the acid precursor and peroxygen source. That is, the composite structure includes the acid precursor and the peroxygen source adhered together. The composite structure can be used with or without a permeable container. When it is desirable to treat a wet surface which requires sanitizing, disinfecting, and/or bleaching, the composite structure can be applied by broadcasting evenly thereto. It is expected that this technique may be advantageous when treating large, wet and rough surfaces. Alternatively, the composite structure can be measured out and added to a container of water for generating a volume of sanitizer solution. The composite structure can additionally include a chemical heater and/or an acid catalyst Peracid Precursor The peracid precursor and the peroxygen source are reactive, in the presence of water, to provide an aqueous peracid sanitizer solution. The peracid precursor preferably remains in solid form at temperatures up to about 40° C. so that under conditions often encountered during transportation and storage, the peracid precursor will remain a solid and will resist reacting with the peroxygen source until a fluid such as water is introduced. Furthermore, the peracid precursor should be one which, when reacted with the peroxygen source, provides a peracid which is soluble in water. Because the peracid precursor and the peroxygen source can be provided together within a permeable container or together in a composite structure, it is desirable that they do not react together until a fluid such as water is introduced.

The peracid precursor is preferably an organic acid. Preferred peracid precursors are compounds containing at least one acyl group which is susceptible to perhydrolysis. Suitable peracid precursors are those of the N-acyl, or O-acyl compound type containing an acyl radical, R—CO— wherein R is an aliphatic group having from 5 to 18 carbon atoms, or an alkylaryl of about 11 to 24 carbon atoms, with 5 to about 18 carbon atoms in the alkyl chain. If the radicals are aliphatic, they preferably contain 5 to 18 carbon atoms and most preferably 5 to 12 carbon atoms.

Preferred peracid precursors are those which can be provided in a solid form under conditions normally encountered during storage of the peracid forming composition, exhibit good water solubility properties, and react quickly with a peroxygen source in the presence of water, and are relatively inexpensive. Preferred peracid precursors include carboxylic acid anhydrides and carboxylic halides. Preferred carboxylic acid anhydrides include maleic acid anhydride, succinic acid anhydride, and glutaric acid anhydride.

The peracid precursor can be provided in either a solid form or a liquid form. It should be understood that reference to "solid" and "liquid" refers to the state of the peracid precursor under temperature conditions normally encountered during storage of the peracid forming composition. In general, solid peracid precursors are those which remain in a solid state at temperatures up to about 40° C. The peracid precursor can be provided in a solid form by techniques similar to those used in the laundry detergent industry. For example, the peracid precursor can be provided in solid form by spray drying liquid slurries, and by granulation techniques using binders such as synthetic or natural polymers or derivatives where blending with binders is followed by extrusion or other techniques. A liquid peracid precursor can be modified so that it is provided in a solid form by adsorbing the acid precursor onto an absorbent or substrate. For example, the peracid precursor can be absorbed into the pores of a powder or other substrate. Preferred substrates which can absorb acid precursor include sodium aluminonsilicates, precipitated silicas, fumed silicas, and diatomaceous earths. A preferred diatomaceous earth material is available under the name Celite. In addition, liquid peracid precursor can be provided in a liquid form and physically isolated from the other components of the peracid forming composition. For example, the liquid peracid precursor can be contained in an envelope which, when physically ruptured, releases the peracid precursor.

Peracid precursors which can be used according to the invention are those which are provided in the solid form, those which are provided in a liquid form but which can be modified into a solid form for use according to the invention, or those which are provided in a liquid form and can be used in a liquid form according to the invention. Exemplary peracid precursors include acetic anhydride, propionic anhydride, butyric anhydride, isobutyric anhydride, valeric anhydride, methylbutyric anhydride, trimethylacetic anhydride, hexanoic anhydride, heptanoic anhydride, octanoic anhydride, nonanoic anhydride, undecanoic anhydride, decanoic anhydride, lauric anhydride, palmitic anhydride, stearic anhydride, docosanoic anhydride, crotonic anhydride, methylacrylic anhydride, oleic anhydride, linoleic anhydride, chloroacetic anhydride, iodoacetic anhydride, dichloroacetic anhydride, trifluoroacetic anhydride, chlorodifluoroacetic anhydride, trichloroacetic anhydride, pentafluoropropionic anhydride, heptafluorobutyric anhydride, succinic anhydride, methylsuccinic anhydride, dimethylsuccinic anhydride, itaconic anhydride, 2-dodecen-1-ylsuccinic anhydride, cis 1,2,3,6-tetrahydrophthalic anhydride, norbomene dicarboxylic anhydride, maleic anhydride, glutaric anhydride, diglycolic anhydride, diethylenetriamine pentaacetic dianhydride, citric anhydride, tetrahydrophthalic anhydride, citraconic anhydride, acetyl chloride, chloroacetyl chloride, trichloroacetyl chloride, propionyl chloride, heptanoyl chloride, octanoyl chloride, nonanoyl chloride, decanoyl chloride, undecanoyl chloride, lauroyl chloride, ethyl chloroformate, ethylene carbonate, propylene carbonate, benzoic anhydride, isatoic anhydride, phthalic anhydride, and mixtures thereof.

Certain peracid precursors which are provided in a liquid form at a temperature of less than about 40° C. can be modified so they can be used as solids. One technique for modifying liquid peracid precursors includes absorbing the liquid peracid precursor into a powder absorbent material. Preferred absorbent materials include precipitated silicas, fumed silicas, aluminosilicates, and diatomaceous earth. The modified liquid peracid precursor can then be dry blended with the remaining components of the peracid forming composition.

Modified liquid peracid precursors may exhibit a relatively high vapor pressure. As a result, peracid precursor vapor may contact the peroxygen source and result in peracid formation. This type of reaction may result in a decreased effectiveness of the peracid forming composition over an extended period of time. In order to increase the shelf life of the peracid forming composition, it may be desirable to coat the modified liquid peracid precursor with a coating that provides a gas or moisture barrier. The modified liquid peracid precursor and/or the peroxygen source can be coated or encapsulated using conventional technology generally known in the coating and encapsulating art. In general, the coating and/or encapsulating can be accomplished in a fluidized bed. Furthermore, it should be appreciated that both the peracid precursor and the peroxygen source can be encapsulated.

The peracid precursor is preferably provided in an amount which will provide a desired level of peracid in the peracid sanitizer for achieving a desired level of sanitizing, disinfecting, and/or bleaching when combined with peroxygen source and water. In general, it is expected that the peracid precursor will be provided in an amount of between about 0.1 wt. % and about 80 wt. % based on the weight of the peracid forming composition. Preferably, the peracid precursor is provided in an amount of between about 2 wt. % and about 30 wt. %, and more preferably between about 5 wt. % and about 20 wt. %.

Peroxygen Source

The peroxygen source reacts with the peracid precursor to provide the peracid sanitizer solution. Preferably, the peroxygen source does not react with the peracid precursor until it is desirable for the components to react together. It is generally desirable for the peroxygen source and the peracid precursor to react together when water is introduced. In addition, the peroxygen source is preferably one which will react with the peracid precursor to provide a peracid reaction product which is soluble in water. The peroxygen source can include inorganic persalts such as sodium perborate, sodium percarbonate, calcium peroxide, sodium peroxide, sodium persulfate, perhydrate of urea, and mixtures thereof. Preferred peroxygen sources include sodium perborate and sodium percarbonate. The sodium perborate component is preferably a monohydrate.

The peroxygen source is preferably provided in an amount which will provide a desired level of peracid in the peracid sanitizer for achieving a desired level of sanitizing, disinfecting, and/or bleaching when combined with acid precursor and water. In general, it is expected that the peroxygen source will be provided in an amount of between about 0.1 wt. % and about 80 wt. % based on the weight of the peracid forming composition. Preferably, the peroxygen source is provided in an amount of between about 2 wt. % and about 30 wt. %, and more preferably between about 5 wt. % and about 20 wt. %.

Chemical Heater

The chemical heater is a component which provides localized heating for accelerating the reaction between peracid precursor and peroxygen source. In general localized heating refers to heating within the container when a container is used. In the case where a container is not used, for example, when the peracid forming composition is in the form of a composite structure which can be applied to a wetted surface, the localized heating refers to the area in sufficient proximity to the acid precursor and the peroxygen source to accelerate the reaction to form peracid sanitizer solution. In the case of providing a composite structure on a wetted surface, the area in sufficient proximity is generally the puddle or droplets of water in which the composite structure is provided. Applicants have found that by providing localized heating, the rate of peracid formation increases. This is demonstrated by example 1.

When the chemical heater is contacted with water, it hydrates and generates heat. As water contacts the chemical heater, the chemical heater generates heat which in turn increases the rate of peracid formation. In general, it is expected that the chemical heater, when present, should be present in an amount sufficient to generate at least about a 5° C. increase in the local temperature. It is expected that the benefit of localized heating will not be very great unless the local temperature is increased by at least about 5° C. Preferably, the local temperature will increase between about 5° C. and about 25° C. It should be appreciated that a higher local temperature increase can be provided at the expense of decreasing the concentration of the peracid precursor, peroxygen source, or acid catalyst for a given volume of peracid forming composition.

A preferred chemical heater can be referred to as a heat generating desiccant. Preferred chemical heaters include zeolites, calcium sulfate, calcium oxide, calcium peroxide, magnesium sulfate, magnesium chloride, magnesium bromide, phosphorous pentoxide, sodium acetate, ferric chloride, ferric bromide, aluminum chloride, and aluminum bromide, aluminum iodide, aluminum sulfate, aluminum iodide, calcium bromide, calcium chloride, ferrous iodide, ferrous sulfate, magnesium iodide, pyrophosphoric acid, zinc chloride, zinc sulfate, and mixtures thereof.

Although water is a preferred trigger for causing the chemical heater to generate heat, other triggers can be used. The chemical heater can generate heat by hydration, hydrolysis, acid-base neutralization, and the like. An exemplary acid-base neutralization includes the combination of sodium hydroxide and citrus acid. Additional acids include those listed below as acid catalysts. Bases which can be used with acid include potassium hydroxide, sodium hydroxide, calcium oxide, aluminum oxide, sodium carbonate and mixtures thereof.

It is generally desirable that the chemical heater is one which will not cause too great of an increase in the pH or provide such a violent rate of heat generation that causes dispersion of the peracid composition or rupture of the permeable container. For example, sodium hydroxide and phosphorous pentoxide ($P_2O_5$) can be considered to be too caustic if used in too great an amount. It should be understood, however, that these components can be used if the pH is controlled so that the aqueous peracid sanitizer solution is provided with a pH of less than about 8, and more preferably less than about 7. In a preferred embodiment of the invention, the aqueous peracid sanitizer solution is provided with a pH of between about 2 and about 4 when corrosion is not a concern. When corrosion is a concern, it is generally desirable to buffer the peracid sanitizer solution near a pH of about 7.

The amount of chemical heater provided in the peracid forming composition is determined by the desired amount of local temperature increase and depends on the selected chemical heater. Certain chemical heaters provide greater generation of heat than others. In general, it is expected that when the chemical heater is incorporated into the peracid forming composition, it will be used in an amount up to about 80 wt. % based on the weight of the peracid forming composition. While a greater amount of chemical heater can be used, it is expected that increasing the amount of chemical heater much beyond 80 wt. % will result in a reduction in the concentration of acid precursor and peroxygen source. Preferably, the chemical heater is provided in an amount of between about 10 wt. % and about 60 wt. %, and more preferably between about 20 wt. % and about 40 wt. %.

Acid Catalyst

The acid catalyst can be provided to accelerate the rate of peracid formation and/or to help maintain the pH of the resulting aqueous peracid sanitizer solution in the range of below about 8, and more preferably below about 7. The acid catalyst is preferably one which remains a solid prior to the peracid forming reaction. The acid catalyst can be a liquid which has been modified to a solid form. In addition, the acid catalyst is preferably a strong acid exhibiting a pKa of less than about 3 and more preferably less than about 1. Of course, it should be appreciated that the system of the invention need not include an acid catalyst. Exemplary acid catalysts which can be used according to the invention include sulfamic acid, citric acid, sodium monohydrogen sulfate, hemi sodium phosphate, aluminum trichloride, iron trichloride, and mixtures thereof.

When the acid catalyst is used, it is preferably used in an amount which provides the desired rate of peracid formation and/or provides the peracid sanitizer with the desired pH. It should be appreciated that the amount of acid catalyst depends on the particular acid catalyst selected. In general, the acid catalyst can be provided in an amount of up to about 20 wt. % based on the weight of the peracid forming composition. Preferably, the acid catalyst is provided in an amount of between about 2 wt. % and about 10 wt. %.

Viscosity Modifier

The peracid forming composition can include a viscosity modifier which has a tendency to increase the viscosity in the localized area created by the reaction of peracid precursor and peroxygen source. In the case where the peracid precursor and peroxygen source react within a permeable container, the interior region of the permeable container can generally be referred to as the localized area. By increasing the viscosity in the localized area, the movement of peracid precursor and/or peroxygen source out of the permeable container is slowed. This results in an increased residence time of the peracid precursor and peroxygen source within the permeable container which provides a greater reaction rate. A preferred viscosity modifier is one which remains solid under normal storage conditions (i.e., at a temperature of less than about 40° C.), remains inert in an oxidizing environment, and exhibits a neutral or acidic pH when dispersed in water.

The viscosity modifier can include natural and synthetic polymers. Preferred viscosity modifiers include xanthun gum, guar gum, acrylic polymers, polyoxyethylene, and mixtures thereof. The viscosity modifier is preferably added in an amount which provides a viscosity within the localized area of between about 300 centipoise and about 2,000 centipoise. The viscosity modifier can be added in an amount of up to about 5 wt %. Preferably, the viscosity modifier is provided in an amount of between about 0.5 wt % and about 2 wt %.

Binder

The composite structure includes both peracid precursor and peroxygen source bound together. In order to bind the peracid precursor and peroxygen source together, a binder can be used. The binder can be the peracid precursor component. Exemplary peracid precursors which can function as binders include glutaric anhydride and maleic anhydride. The binder can additionally include other components such as alcohol ethoxylates and homopolymers and/or copolymers of ethylene oxide and/or propylene oxide. Preferred alcohol ethoxylates include $C_{12}$–$C_{15}$ fatty alcohol ethoxylates and $C_{14}$–$C_{15}$ fatty alcohol ethoxylates with 5 moles of ethoxylation. In addition, preferred ethylene oxide polymers include polyethylene glycol of molecular weight of about 8,000 and polyethylene glycol methyl ether of molecular weight of about 750.

The composite structure is preferably prepared by a method which avoids or minimizes the reaction of peracid precursor and peroxygen source. In general, this method preferably takes place in the general absence of water. The peracid precursor and peroxygen source can be mixed with molten binder. The resulting composition can be cooled to provide a solid, then crushed and sieved to provide an composite composition. U.S. Pat. No. 5,670,684, which is incorporated herein by reference, describes a process for utilizing a hot melt binder. This process can be used to provide a composite composition according to the present invention.

Moisture Barriers

Moisture barriers can be provided coating the composite structure or a component of the composition to reduce the penetration of the solvent vapor into the component. In particular, it is desirable to restrict the penetration of water vapor from contacting the peracid precursor and/or peroxygen source. Accordingly, the peracid precursor, peroxygen source, or composite structure can be coated with a moisture barrier. Exemplary materials which can be provided as moisture barriers include monoethanol amides of stearic acid, magnesium stearates, calcium stearates, polyethylene glycols, alcohol ethoxylates, ethylene bis-stearamides, mono and dihexadecyl phosphate esters, and mixtures thereof. Preferred polyethylene glycols have a molecular weight of about 20,000 to about 200,000. Particularly preferred polyethylene glycols have molecular weights of about 50,000 to 100,000. Preferred alcohol ethoxylates include $C_{14}$–$C_{15}$ fatty alcohol ethoxylates with five moles of ethoxylation and $C_{12}$–$C_{15}$ fatty alcohol ethoxylates with 12 moles of ethoxylation.

Permeable Container

The permeable container is provided to contain the peracid forming composition prior to introduction of the system into an aqueous solution. Accordingly, the permeable container is permeable to water. That is, water can flow into the permeable container and peracid solution can flow out of the permeable container.

The permeable container can be any material which holds the peracid forming composition together and which is permeable to water and peracid solution. Preferred materials which can be used to form the permeable container include cellulosic material such as paper or tissue. The material forming the container can be characterized as a membrane. The permeable container can be constructed from cellulosic membranes such as those available under the name Precision Wipe from Kimberly Clark, or a two-phase heat-sealed tissue such as grade 1234T from Dexter Corp. In addition, the permeable membrane can be manufactured from a soluble membrane, such as, polyvinyl alcohol, which will dissolve in water.

Figure 1:
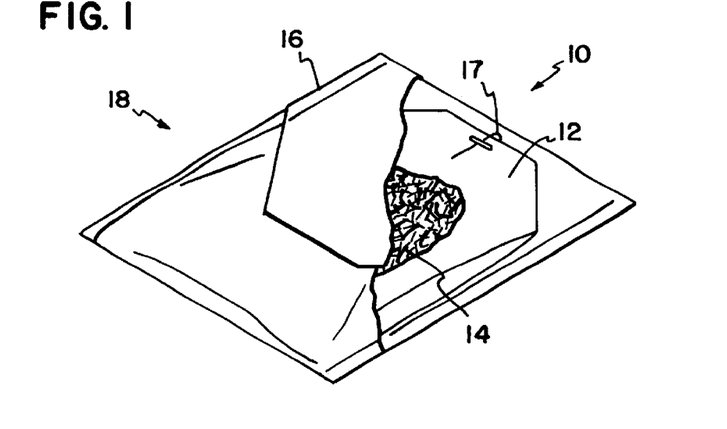
FIG. 1 is a partial cutaway, perspective view of a system for forming and releasing aqueous peracid solution according to the principles of the present invention.

Now referring to FIG. 1, a system for forming and releasing an aqueous peracid sanitizer solution is indicated at reference numeral 10. The system 10 includes a container 12 and a peracid forming composition 14 provided within the container 12. The container 12 is permeable to the passage of water and an aqueous peracid sanitizer solution. Preferably, the container 12 is provided within an envelope 16 which is relatively moisture impermeable. Accordingly, the envelope 16 prevents humidity from entering into the peracid forming composition 14. When the envelope 16 is opened, the container 12 can be removed and placed in water. A line 17, such as a string, can be provided to assist removing the spent system from the sanitizing solution.

The combination of the container 12 and the peracid forming composition 14 can be referred to as a package 18. In general, the size of the package 18 can be adjusted for providing the desired size or strength of sanitizing solution. For example, the package 18 can be sized to provide one gallon of sanitizing solution. Accordingly, any multiple of one gallon of sanitizing solution can be provided by incorporating the corresponding number of packages. For example, five gallons of sanitizing solution can be prepared by introducing five packages into a five-gallon container of water. Because it is expected that the system of the invention will be advantageously used by household consumers, each package can advantageously provide a small amount of sanitizing solution.

It is an advantage of the invention that the peracid forming composition is more stable than commercially available aqueous peracid sanitizer solutions. In addition, the peracid forming composition of the invention is easy to use and provides a reduction in packaging size and shipping cost compared with commercially available aqueous peracid sanitizer solutions. Furthermore, the invention provides for the enhanced rate and yield of peracid formed from the peracid forming composition.

Figure 2:
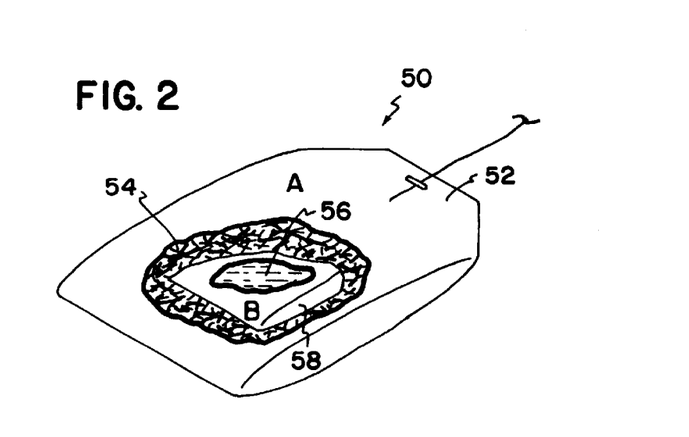
FIG. 2 is a partial cutaway, perspective view of an alternative embodiment of a system for forming and releasing an aqueous peracid solution according to the principles of the present invention.

Now referring to FIG. 2, an alternative system for forming and releasing an aqueous peracid sanitizer solution is indicated reference 50. The article 50 includes a container 52, a first peracid forming component 54, and a second peracid forming component 56 which is provided within a rupturable container 58. The first peracid forming component 54 and the second peracid forming component 56, when contacted, generate peracid. The rupturable container 58 is provided to keep the components 54 and 56 from contacting each other. Accordingly, just before the article 50 is placed in water, the rupturable container 58 can be ruptured thereby releasing the second peracid forming component 56. Alternatively, the rupturable container 58 can be allowed to degrade thereby releasing the second peracid forming component 56. In most situations, it is expected that the second peracid forming component 56 within the rupturable container 58 is a peracid precursor, especially, a liquid peracid precursor.

Figure 3:
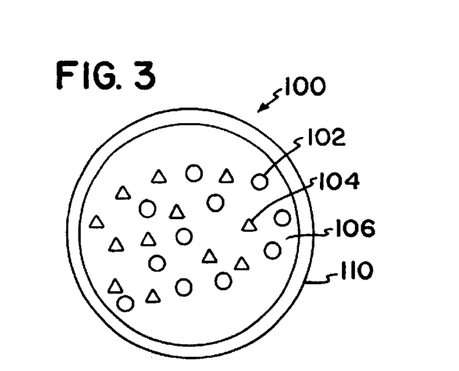
FIG. 3 is a diagramatic view of a composite structure for forming and releasing an aqueous peracid solution according to the principles of the present invention.

Now referring to FIG. 3, a composite structure is shown at reference 100. The composite structure 100 includes a first peracid forming component 102 and a second peracid forming component 104 held together by a binder 106. It should be appreciated that the binder 106 and one of the peracid forming components 102 or 104 can actually be the same material. A protective coating 110 can be provided enclosing the composite structure. Preferably, the protective coating 110 preferably acts as a moisture barrier to prevent humidity from causing the peracid forming components to react. It should be appreciated that the protective coating can be omitted. If a protective coating is not provided, it is desirable to limit the ability of moisture to enter the composite structure by providing, for example, an envelope or moisture barrier such as provided in FIG. 1. While envelope or coating type moisture barriers are preferred, other types of containers can be used to limit or reduce moisture from contacting the composition.

Figure 4:
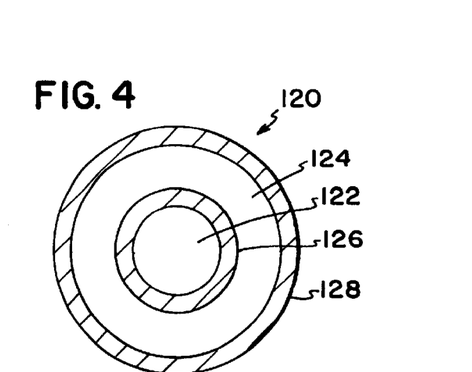
FIG. 4 is a diagramatic view of an alternative embodiment of a composite structure for forming and releasing an aqueous peracid solution according to the principles of the present invention.

Now referring to FIG. 4, an alternative embodiment of a composite structure according to the invention is indicated at reference 120. The composite structure 120 includes a first peracid forming component 122, a second peracid forming component 124, and a binder 126 for holding the first peracid forming component 122 and the second peracid forming component 124 together. In addition, a protective coating 128 can be provided as a moisture barrier. It should be understood that the protective coating 128 is optional.

The system and the composite structure can be used for sanitizing, disinfecting, and/or bleaching different types of surfaces. The system is preferably used when it is desirable to generate a quantity of sanitizer solution. This quantity of sanitizer solution has particular use for hard surface disinfection, potable water disinfection, food surface sanitization including fruit, vegetables and meat, medical instrument sterilization, and kitchen (third sink) sanitizer. The composite structure, when used without a permeable container, can preferably be used to generate sanitizer solution at a particular location. For example, the composite structure can be used as a biohazard cleanup powder, a carpet sanitizer powder, floor powder for a walk-in freezer, and ostomy deodorizer. For example, it may be easier to clean certain types of surfaces by generating the sanitizer solution on that surface, rather than trying to apply the sanitizer solution to the surface.

Example 1

Four test compositions identified as A–D were prepared and tested. The components of each composition include glutaric anhydride, sodium perborate, sulfamic acid, and magnesium sulfate. The parts by weight of each component for each test composition is identified in Table 1.

TABLE 1

| Test | Glutaric Anhydride | $NaBO_3$ $H_2O$ | Sulfamic Acid | $MgSO_4$ | Permeable Container | Grams |
| --- | --- | --- | --- | --- | --- | --- |
| A | 2.5 | 2.0 | 4.0 | 6.0 | No | 14.5 |
| B | 2.5 | 2.0 | 4.0 | 6.0 | Yes | 14.5 |
| C | 2.5 | 2.0 | 4.0 | 0.0 | Yes | 8.5 |
| D | 2.5 | 2.0 | 4.0 | 12.0 | Yes | 20.5 |

Test composition A is a control where the composition was added directly to 1000 ml of deionized water without the use of a permeable container. Test compositions B–D were enclosed in paper wipe available as Precision Wipe from Kimberly-Clark. The permeable containers were prepared by folding the paper wipe, taping and stapling. Each permeable container containing a test composition was immersed in 1000 ml of deionized water. The permeable containers were provided having a dimension of about 4.5 inches by 8.25 inches.

For each test, a 10.0 gram aliquot of solution was removed at time intervals of 5, 15, and 30 minutes and diluted into 90 ml of deionized water, which was further diluted by a factor of 5 to achieve total dilution of 50X. The 50X solutions were assayed for peracid using the method described below. The results are reported in Table 2.

TABLE 2

| | | 5 minutes | | 15 minutes | | 30 minutes | |
| --- | --- | --- | --- | --- | --- | --- | --- |
| Test | $MgSO_4$ | Drops of titrant | ppm POAA | Drops of titrant | ppm POAA | Drops of titrant | ppm POAA |
| A (no permeable container) | 6.0 | 2 | 19 | 2 | 19 | 2 | 19 |
| B | 6.0 | 6 | 121 | 9 | 197 | 11 | 248 |
| C | 0.0 | 4 | 70 | 6 | 121 | 7 | 146 |
| D | 12.0 | 8 | 172 | 10 | 1050 | 12 | 274 |

Figure 5:
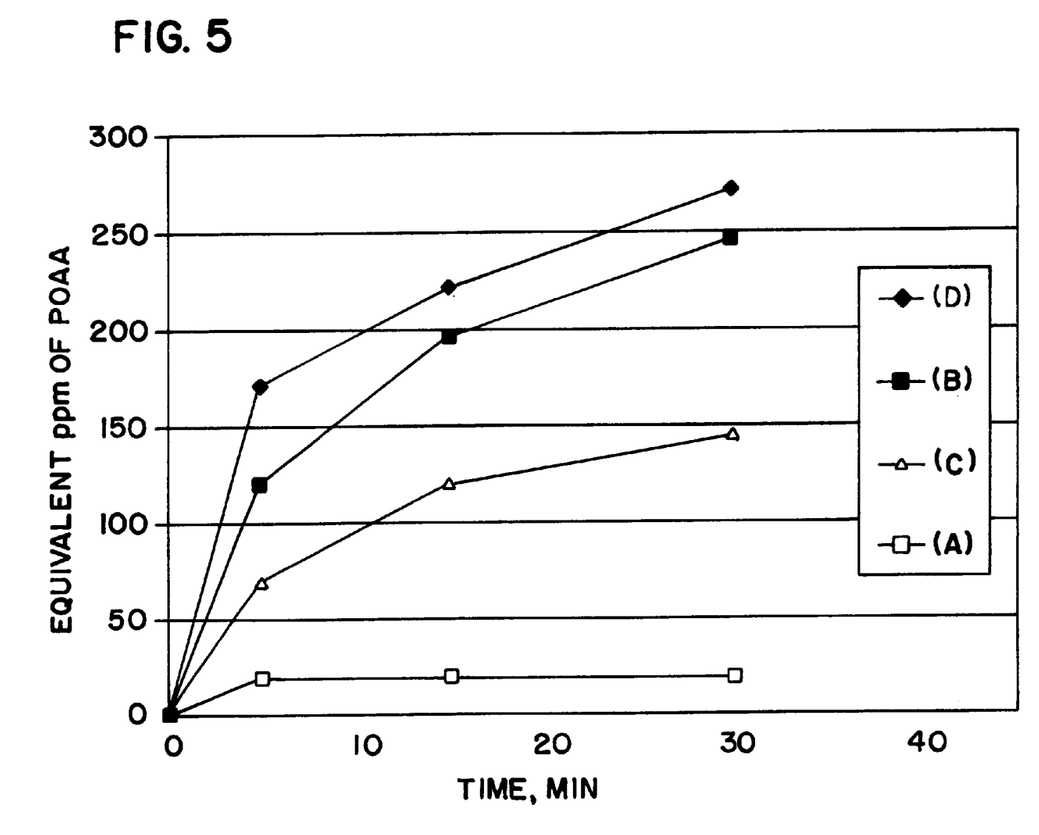
FIG. 5 is graph showing the rate of peracid formation for test compositions identified in example 1.

The data in Table 2 is graphed in FIG. 5. The data shows the benefit of using a permeable container, and a chemical heater, for increasing the rate of aqueous peracid sanitizer solution formation. The peracid level was determined by an iodometric titration method. 20 g of sample was added to a plastic vial with a micro stir bar and with rapid stirring. Then 5 drops of reagent (10% KI) was added, followed by 5 drops of (59% $H_3PO_4$), followed by 5 drops of indicator (2% starch indicator). The three reagents above were added within 30 seconds with vigorous stirring. The titration with 0.08% $Na_2S_2O_3$ solution followed immediately, yielding the number of drops needed to make the iodine-starch blue color disappear. Calibration was done with a known peracetic solution (KX6091, 11.4% POAA or peroxyacetic acid), which yielded the calibration curve:

Equivalent POAA in ppm=0.508×(drops of 0.08% Na2S2O3)+ 1.275

Figure 6:
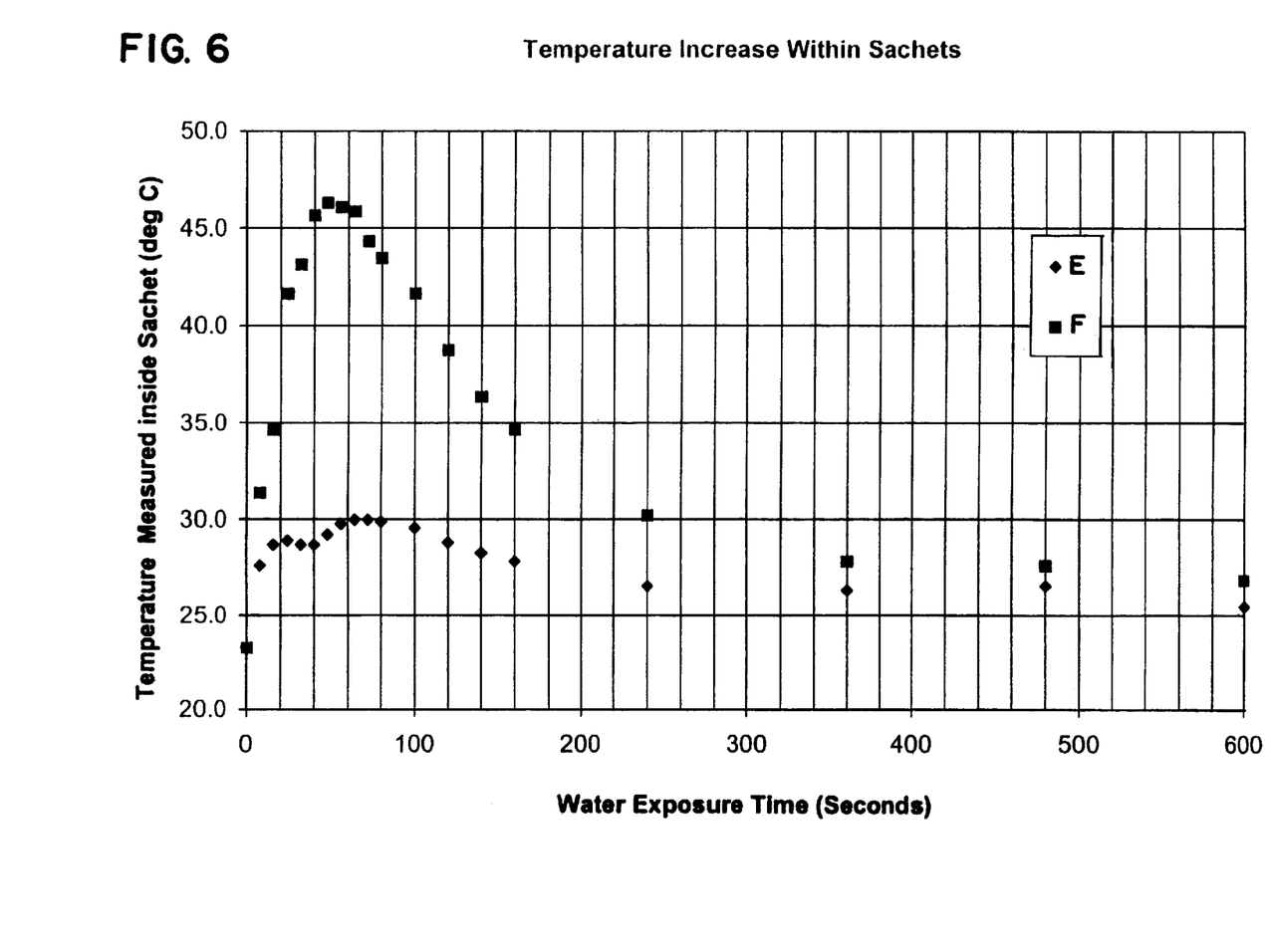
FIG. 6 is a graph showing the temperature increase for test compositions identified in example 1.

To demonstrate the effectiveness of $MgSO_4$ as a chemical heater, the following two formulas were packaged in permeable containers and immersed in 1.0 L of deionized water. The temperature profiles were recorded using a low heat capacity thermistor embedded in the body of the powder within the sachets. The results are reported in FIG. 6. The composition and the temperature differential is reported in Table 3.

TABLE 3

| Test | Succinic Anhydride | $NaBO_3$ $H_2O$ | Sulfamic | $MgSO_4$ | Sachet | Grams | ΔT ° C. |
|---|---|---|---|---|---|---|---|
| E | 2.5 | 2.0 | 4.0 | 6.0 | Yes | 14.5 | 7 |
| F | 2.5 | 2.0 | 4.0 | 12.0 | Yes | 20.5 | 26 |

EXAMPLE 2

This example demonstrates the use of an active ingredient as a binder for forming a composite structure.

| | |
|---|---|
| Glutaric anhydride | 10 g |
| Mg $SO_4$ (granular, anhydrous) | 12 g |
| Sodium perborate monohydrate | 5 g |

Glutaric anhydride was added molten (57° C.) to the dry blend of the remaining two components. After cooling to room temperature, the fused composite was crushed and sieved to provide a size of between 16 and 10 mesh (US Standard Testing Sieve, particle size range is between 1.18–2.00 mm).

The following procedure was used to evaluate the localized reaction. To simulate application of the particles on wet, porous surfaces such as soil or soiled floor, we applied the composite structure by broadcasting onto a multi-well tray, the wells being partially filled with water, and let stand for a period of time. The wells were emptied and rinsed and the pooled solution was titrated for peracid. For control, the same quantity of the formulation in a powder blend was broadcast and assayed in the same manner.

For 110 mg samples broadcast over 96 wells, each having about 0.17 g of water, and with 1000 ml total pool, the assay results were:

ppm POAA

| | |
|---|---|
| Composite structure | 14.5 |
| Powder blend | 4.8 |

EXAMPLE 3

This example demonstrates that liquid peracid precursors can be incorporated into powder absorbent materials such as precipitated silicas, fumed silicas, aluminosilicates, and diatomaceous earth. Preferably, the liquid precursor is incorporated into the powder absorbent materials prior to blending with the remaining components of the peracid forming composition.

2.48 g of a (2:1 w/w) mixture of acetic anhydride and acetic acid was absorbed onto 0.82 g precipitated silica (Sipernet 50 from Degussa), which was blended with 2.0 g of Sodium perborate monohydrate, 4.0 g of sulfamic acid and 6.0 g of magnesium sulfate. The total 15.3 g of this formulation was enclosed in a permeable container made of nonwoven cellulosic membrane (Precision Wipe from Kimberly Clark). The permeable container containing peracid forming composition was immersed in 1,000 ml of DI water at ambient temperature. 83 ppm of POAA was found after 10 minutes of dipping time, and 180 ppm was found after 30 minutes.

The above specification, examples and data provide a complete description of the manufacture and use of the composition and article of the invention. Since many embodiments of the invention can be made without departing from the spirit and scope of the invention, the invention resides in the claims hereinafter appended.

We claim:

1. A system for forming and releasing an aqueous peracid solution, the system comprising:
   (a) a peracid forming composition comprising:
      (i) a peracid precursor;
      (ii) a peroxygen source;
      (iii) a chemical heater capable of releasing heat upon hydration provided in an amount sufficient to generate a local solution temperature increase of at least about 5° C. after immersion of the system in water; and
   (b) a container for containing said peracid forming composition, said container being permeable to the passage of water and aqueous peracid solution; and
   wherein the system, when immersed in water, generates an aqueous peracid sanitizer solution having a pH of less than 8.

2. A system according to claim 1, wherein the system, when immersed in water, generates an aqueous peracid solution having a pH of between about 2 and about 4.

3. A system according to claim 1, wherein the peracid forming composition further comprises an acid catalyst.

4. A system according to claim 3, wherein the acid catalyst comprises sulfamic acid.

5. A system according to claim 1, wherein the chemical heater comprises hydratable salt.

6. A system according to claim 5, wherein the hydratable salt comprises a salt of an organic acid.

7. A system according to claim 5, wherein the hydratable salt comprises a salt of a mineral acid.

8. A system according to claim 5, wherein the hydratable salt comprises magnesium sulphate.

9. A system according to claim 5, wherein the hydratable salt comprises an alkali earth metal salt.

10. A system according to claim 1, wherein the peroxygen source comprises sodium perborate.

11. A system according to claim 1, wherein the peracid precursor comprises carboxylic acid anhydride.

12. A system according to claim 11, wherein the carboxylic acid anhydride comprises at least one of glutaric acid anhydride, succinic acid anhydride, and maleic acid anhydride.

13. A system according to claim 1, wherein the peracid precursor comprises carboxylic acid halide.

14. A method of sanitizing a surface having a population of microorganisms, the process comprising steps of:

combining a system for forming and releasing an aqueous peracid solution with water to provide an aqueous peracid sanitizer solution, the system for forming and releasing an aqueous peracid solution comprising:
(a) a peracid forming composition comprising:
(i) a peracid precursor;
(ii) a peroxygen source; and
(iii) a chemical heater capable of releasing heat upon hydration provided in an amount sufficient to generate a local solution temperature increase of at least 5° C. after immersion of the system in water; and
(b) a container for containing said peracid forming composition, said container being permeable to the passage of water and aqueous peracid solution; and contacting a surface having a microbial population with the aqueous peracid sanitizer solution for sufficient period to substantially reduce the population of microorganisms on the surface.

* * * * *